United States Patent
Centers et al.

[19]

[11] Patent Number: 5,889,200
[45] Date of Patent: *Mar. 30, 1999

[54] TANDEM TECHNIQUE FOR FLUID MONITORING

[75] Inventors: Phillip W. Centers, Dayton; Costandy S. Saba, Springfield; James D. Wolf, Kettering, all of Ohio

[73] Assignee: The University of Dayton, Dayton, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 707,966

[22] Filed: Aug. 30, 1996

[51] Int. Cl.$^6$ ............................. G01N 27/02; G01N 33/26
[52] U.S. Cl. ...................... 73/53.01; 73/53.05; 73/53.07; 73/61.42; 73/61.71; 324/693; 324/698
[58] Field of Search ............................. 73/53.01, 53.05, 73/53.06, 53.07, 61.41, 61.42, 61.71; 324/71.1, 691, 693, 698, 713

[56] References Cited

U.S. PATENT DOCUMENTS

| | | | |
|---|---|---|---|
| 3,686,926 | 8/1972 | Miller et al. .......................... | 324/698 X |
| 4,029,554 | 6/1977 | Ellison ................................ | 324/71.1 X |
| 4,030,028 | 6/1977 | Allender ................................ | 324/698 |
| 4,146,437 | 3/1979 | O'Keefe . | |
| 4,317,705 | 3/1982 | Hamada et al. . | |
| 4,654,126 | 3/1987 | Amelio et al. . | |
| 4,686,857 | 8/1987 | Kato ...................................... | 324/698 X |
| 4,744,870 | 5/1988 | Kauffman .............................. | 436/60 X |
| 4,764,258 | 8/1988 | Kauffman .............................. | 436/60 X |
| 4,928,065 | 5/1990 | Lane et al. . | |
| 5,071,527 | 12/1991 | Kauffman ............................ | 324/439 X |
| 5,089,780 | 2/1992 | Megerle .............................. | 324/698 X |
| 5,537,336 | 7/1996 | Joyce .................................. | 73/53.05 X |
| 5,644,239 | 7/1997 | Huang et al. ........................ | 324/698 X |

*Primary Examiner*—Daniel S. Larkin
*Attorney, Agent, or Firm*—Killworth, Gottman, Hagan & Schaeff, L.L.P.

[57] ABSTRACT

The present invention relates to a method and apparatus which can be used to detect the abnormal operating condition of equipment, such as engines and machinery, the usefulness of the fluid, and the content of wear metals and elemental constituents in the fluid. The method comprises the steps of bringing at least two electrodes into contact with a sample of a fluid to be analyzed; applying a square voltage wave form to the electrodes at a predetermined scan range and scan rate to cause a current to flow between the electrodes; monitoring the current at the electrodes to determine a current output signal; using the current output signal to measure the conductivity of the fluid; and analyzing the sample to determine a content of wear metals and elemental constituents in the sample.

15 Claims, 6 Drawing Sheets

TANDEM TECHNIQUE FOR FLUID MONITORING

The United States Government has rights in this invention pursuant to Contract No. F33615-93-C-2307 awarded by the Department of the Air Force.

CROSS REFERENCE TO RELATED APPLICATIONS

Reference is made to copending application Ser. No. 08/707,965, filed contemporaneously herewith, and entitled "Single Electrode Conductivity Technique", the disclosure of which is hereby incorporated by reference.

BACKGROUND OF THE INVENTION

The present invention relates generally to a method and apparatus for evaluating fluids and, more specifically, to a method and apparatus employing a conductivity sensor comprising at least two electrodes for the analysis of fluids subject to degradation and/or contamination and a spectrometer to detect the presence of wear metals and elemental constituents in the fluid.

Fluids, such as oils, lubricants, and other similar fluids are used in ways that cause their degradation. For example, it is common to lubricate and cool the components of operating equipment by wetting those components with an oil or lubricant. As the oil or lubricant performs its functions, it experiences environmental stresses which cause its base stock to degrade. As another example, oils used as transmission fluids and in hydraulic systems are subjected to stresses such as pressure, frequent movements, and heat. Stresses such as these also degrade the fluid.

Since it is undesirable to use a fluid beyond its useful life, an equipment operator will monitor a fluid and establish scheduled fluid changes for the equipment. The length of operating time between scheduled changes is chosen conservatively so that a fluid, which is beyond its useful life, does not remain in the equipment and damage the equipment. Unfortunately, this conservative approach results in fluids which still have useful lives being discarded. This approach also will not provide the operator with an indication of whether the equipment is operating properly.

Fluid condition monitoring is a technique that involves the analysis of a fluid in field use for the purpose of assessing either its level of degradation or its residual capacity to perform some important tribological function. The condition of the used fluid is determined by detecting changes in certain chemical or physical properties of the fluid caused by degradation of the fluid base stock or depletion of the additive package. For properly running equipment, the physical properties or chemical compositions of the fluid change at a certain rate, generally quite minimally, until the additive package is depleted. Changes in equipment parameters or conditions which can affect the fluid itself may or may not be coincident with changes in the level of wear debris in the fluid. For example, a fluid ages or degrades in normal operations, sometimes to an unacceptable level without any abnormal operation, of the equipment. Thus, monitoring can be used to assist in the determination of the proper interval for fluid changes.

When abnormal operating conditions occur, e.g., an increase in aeration rate of the fluid (caused by excessive seal leakage, deteriorated "O" ring, cracked diffuser cases, etc.) and/or an increase in fluid temperature, the rate of fluid degradation increases and the physical properties and chemical composition of the fluid change commensurately. In these cases, fluid monitoring can identify abnormally operating equipment which cannot be identified by the more frequently encountered monitoring of wear debris. In these situations, detections of fluid condition supplement wear metal analysis in detection of atypical mechanical system operation.

U.S. Pat. No. 4,029,554 to Ellison teaches an oil analysis method and an apparatus, known as Complete Oil Breakdown Rate Analysis (COBRA), for detecting when an oil is approaching the end of its useful life. In this method, a sample of oil is placed between two electrodes and an electric current is applied to the oil. The current causes an oxidation reaction to take place at one of the electrodes to form an oxide on one of the electrodes. This oxidation reaction produces a corresponding voltage output across a resistor and the output is measured. The greater the concentration of oxidation by-products present in the oil, the less resistance between the electrodes and the greater the current produced.

U.S. Pat. Nos. 4,744,870 and 4,764,258 to Kauffman, which are both assigned to the assignee of the present invention, disclose methods for determining the remaining useful life of fluids. These methods are fast, accurate, easy to operate and can be performed with inexpensive equipment. In these methods, fluid samples are mixed with a solvent and an electrolyte in either an organic base or a solid substrate, depending on the type of fluid which is being tested. A sample of fluid is removed from the system, placed in an electrolytic cell and subjected to a cyclic voltammetric analysis. The current generated during the cyclic voltammetric analysis is measured and recorded. The remaining useful life of the fluid is then determined from the oxidation or reduction wave height.

U.S. Pat. No. 5,071,527, also to Kauffman and assigned to assignee of the present invention, provides a more complete fluid analysis, including on-line analysis, which measures antioxidant depletion, oxidation initiator buildup, product buildup, and liquid contamination. The method uses a triangular wave form which is applied to a microelectrode. The resulting current is monitored at a second microelectrode. In high resistance fluids, such as oils, fuels, etc., a third electrode is used as a reference voltage for the applied voltage wave form. This technique uses a voltage range of about ±120V to cause electro-oxidation of antioxidants and electro-reduction of hydroperoxides and other thermal-oxidation products. The current flow produced by the electro-chemical reactions is then used to monitor the remaining useful life of the monitored fluid.

While the above techniques provide useful fluid analyses, they are stand alone analytical tools that provide a single data point that could only relate to changes in the condition of the lubricant. Thus, a need exists for a fluid analysis technique which requires less circuitry, can be conducted off-line, requires less time, and can be used in conjunction with other supplementary oil analysis techniques. Further, the above methods do not provide a method for analyzing the concentration of wear metals and elemental constituents in the fluid. Thus, a need also exists for a method which can simultaneously determine the content of wear metals and elemental constituents in the fluid and the condition of the lubricant.

SUMMARY OF THE INVENTION

The present invention provides a fluid analysis technique which measures the level of degradation, whether the fluid has become contaminated and the concentration of wear metals and/or elemental constituents in the fluid. The method includes using a conductivity sensor, having at least two electrodes, to analyze a sample of the fluid. In a preferred embodiment, the conductivity sensor comprises a plurality of electrodes which are arranged in an interlaced network. After the conductivity analysis has been completed, the sample is then analyzed using a spectrometer to measure the content of wear metals and/or elemental constituents in the fluid. The conductivity sensor can be inserted into or can be a part of the sample reservoir of the spectrometer.

The method measures the conductivity of a fluid to determine the level of degradation of the fluid and to detect leaks into the equipment in which the fluid is used. As a fluid degrades, its conductivity gradually increases. When the conductivity of the fluid exceeds a predetermined value, then the condition of the fluid is indicative of alarming changes in equipment parameters or conditions. When a leak exists in the system, highly conductive liquids come into contact with the fluid in the equipment. These liquids cause a rapid increase in the conductivity of the fluid indicating their presence. By monitoring the condition of the fluid, the equipment operator will be better able to determine when the fluid should be changed or when the equipment is experiencing abnormal operating conditions.

Once the conductivity analysis of the fluid has been completed, a spectrometric analysis is performed to detect the presence of wear metals and elemental constituents in the fluid. Under normal operating conditions, certain levels of metal concentrations are generated. Wear metals are generally dissolved or submicron in size. However, for abnormally operating equipment, wear metal level and size increase beyond an acceptable level. Spectrometric analysis can generally determine the trend in wear metal increase, and can detect abnormally wearing gears, bearings, or any other oil wetted components of the equipment.

Specifically, the method comprises the steps of bringing at least two electrodes into contact with a sample of a fluid to be analyzed; applying a square voltage wave form to the electrodes at a predetermined scan range and scan rate to cause a current to flow between the electrodes; monitoring the current at he electrodes to determine a current output signal; using the current output signal to measure the conductivity of the fluid; and analyzing the sample to determine a content of wear metals and elemental constituents in the sample.

DETAILED DESCRIPTION

To detect the conductivity of a fluid, a square voltage wave form is applied to a conductivity sensor containing at least two electrodes. The current that flows between the electrodes is monitored. The square wave form produces a continuous current output eliminating the need for peak hold circuitry. The voltage applied to the electrode of the conductivity sensor is less than ±10V to insure the monitored current is based entirely on the fluid's conductivity. Voltages greater than ±10V could cause oxidation-reduction reactions to take place in the fluid which make it difficult to determine the conductivity of the fluid.

The conductivity of a sample of the fluid is measured using the conductivity sensor. The conductivity sensor measures the conductivity of the fluid sample to determine the degradation level of the fluid and to detect whether the fluid has become contaminated. After the conductivity of the fluid has been measured, the fluid is analyzed to determine the content of wear metals and/or elemental constituents in the fluid. Preferably, this analysis takes place in a spectrometer.

Once the conductivity measurements have been taken and the content of the wear metals and elemental constituents has been determined, the results of the tests are analyzed. The measured conductivity values are compared to previously derived data and to standardized values for the particular fluid for which the conductivity is being measured. The exact data and values chosen for the comparison depend upon the type of fluid, the type of oxidant in the fluid, fluid consumption rates and other factors. These standard values can be determined by means of testing the fluid and the particular equipment in which the fluid is being used. Any deviation from the standard values is indicative of thermal and oxidative stressing of the fluid. Once the conductivity measurement for the fluid equals or exceeds the standardized value for that particular fluid, the operator then knows that the fluid is experiencing abnormal operating conditions. As with the conductivity analysis, the spectrometric analysis results for the fluid are compared to standardized values or threshold values for the equipment and any deviation from the acceptable limits is indicative of wearing components in the equipment.

Figure 1:
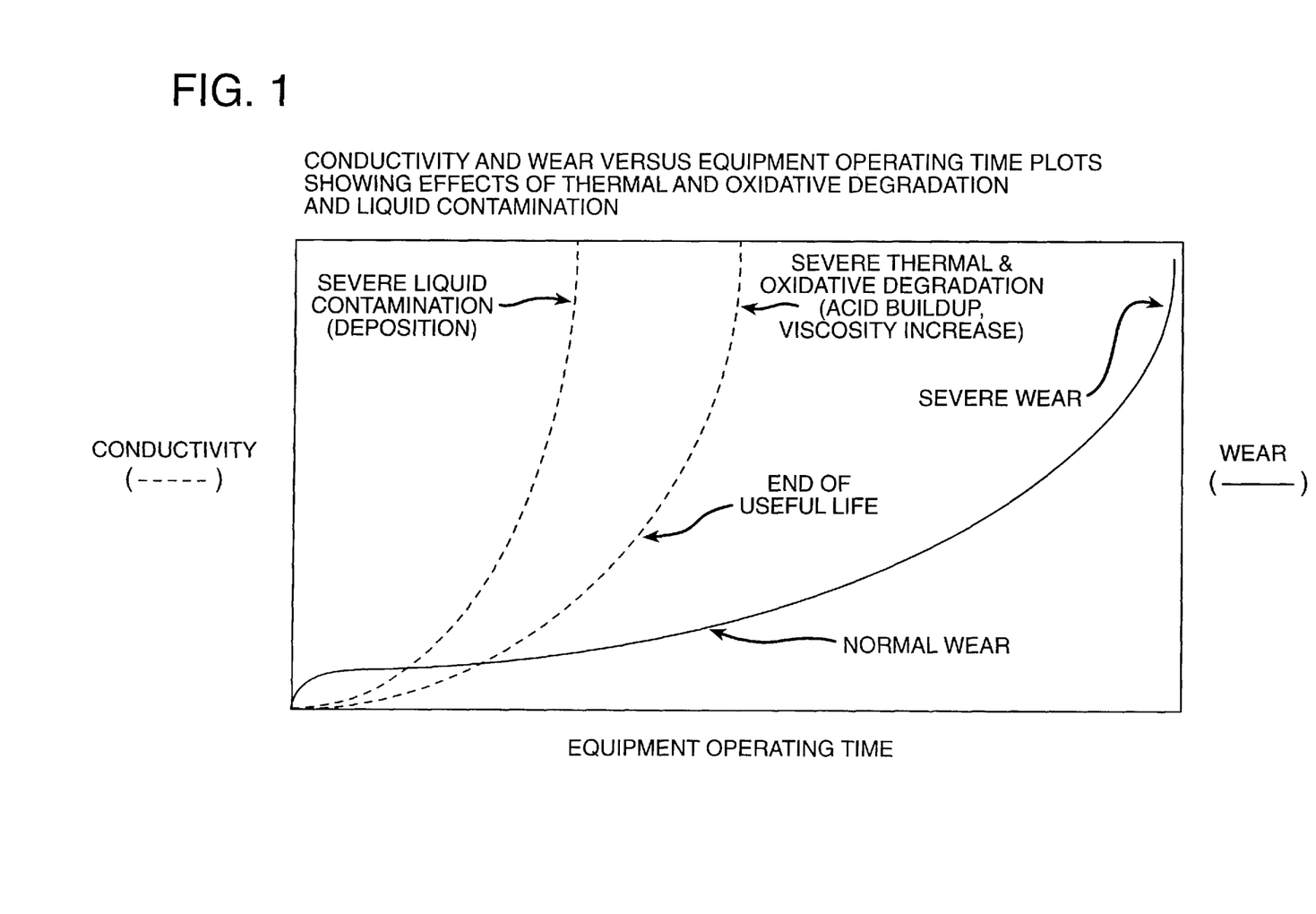
FIG. 1 is a plot of conductivity and wear versus equipment operating time showing the effects of thermal and oxidative degradation and liquid contamination.

FIG. 1 shows simulated plots showing the effects of temperature and oxidation of a fluid and component wear on equipment life. The plot shows conductivity and wear versus operating time. The dashed line represents conductivity curves while the solid line represents a wear curve. As can be seen in FIG. 1, a fluid degrades gradually over time. Abnormal operating conditions can accelerate viscosity increases and acid and coke build up. These parameters in the fluid gradually cause an increase in conductivity of the fluid. When the conductivity of the fluid reaches the point of rapid increase, the equipment must be examined for leaks, usually due to broken seals and problems should be corrected to prevent equipment failure.

In contrast to the degradation of a fluid, liquid contamination in the equipment causes an immediate and dramatic increase in the conductivity of the fluid. When other leaks exist in the system, highly conductive liquids come into contact with the system contaminating the fluid. As can be seen in FIG. 1, once the fluid becomes contaminated, these highly conductive liquids almost immediately cause a rapid increase in the conductivity of the fluid. Such a rapid increase in the conductivity of the fluid indicates, especially if the fluid has just recently been changed, that the fluid has become contaminated and should be replaced. This rapid increase also indicates that the equipment should be checked for the presence of a leak. Another factor such as high temperatures beyond normal operating conditions can cause increases in the conductivity of the fluid. Hot spots can develop where the oil thermally decomposes, causing deposit formation. These deposits can flake off and clog nozzles, preventing oil from reaching bearings. As a result bearings may starve and seize. Thus, by monitoring the conductivity of a particular fluid and comparing that conductivity value to standardized values for that fluid, one can determine the remaining useful life for that fluid and whether that fluid has become contaminated.

Figure 2:
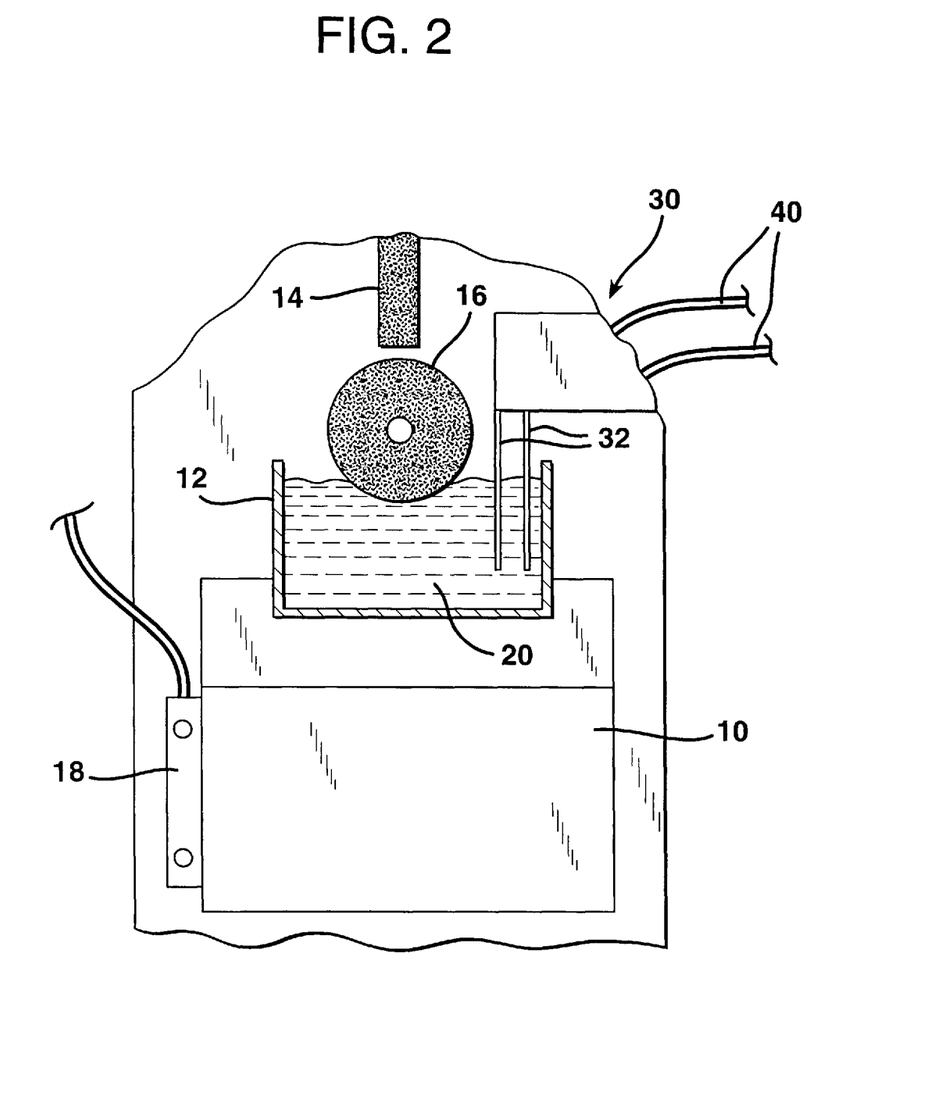
FIG. 2 shows a schematic of one embodiment of this invention in which the conductivity sensor is mounted in an emission spectrometer.

FIG. 2 shows a schematic view of one embodiment of this invention in which the conductivity sensor is used in conjunction with an atomic emission spectrometer 10. Spectrometer 10 includes a sample reservoir 12, a rod electrode 14, a disk electrode 16, and a platform sensor 18. A sample of fluid 20 is placed into and contained in sample reservoir 12. A conductivity sensor 30 comprising at least two electrodes 32 is inserted into sample 20. The dimensions of conductivity sensor 30 are such that sensor 30 neither interferes with nor blocks the optical path of spectrometer 10. Conductivity sensor 30 can be mounted on a spindle on a conventional sample stand to allow sensor 30 to be inserted vertically into sample reservoir 12 and moved out of the testing position to permit placement of another fluid sample into sample reservoir 12. Conductivity sensor 30 may optionally include a proximity switch (not shown) which initiates the conductivity test when sensor 30 is inserted into sample 20. Leads 40 connect sensor 30 to a controller which controls the operation of sensor 30 and platform sensor 18 of spectrometer 10. Sensor 30 does not interfere with the operation of disk electrode 16 nor does it come into contact with the sides of sample reservoir 12 of spectrometer 10.

Platform sensor 18 senses the proximity of sample reservoir 12 to disk electrode 16. Once sample reservoir 12 reaches a certain distance from disk electrode 16, sensor 18 signals the controller to disconnect the electrical supply to electrodes 32. This protects electrodes 32 from the current generated by spectrometer 10 as it analyzes sample 20. Platform sensor 18 is linked by a relay board to an interlock system of spectrometer 10 which prohibits operation of conductivity sensor 30 and spectrometer 10 simultaneously.

Electrodes 32 of conductivity sensor 30 are formed from a highly conductive material, such as copper, suitable copper alloys, nickel and suitable nickel alloys, or stainless steel, and are mounted on a nonconductive substrate. Electrodes 32 can have a width which ranges between about 10 microns and about 10 millimeters. Electrodes 32 are spaced apart from one another by a distance equivalent to their widths. The sensitivity of sensor 30 depends upon the surface area of sensor 30 which in turn is proportional to the lengths and widths of electrodes 32. Generally, an increased area of electrodes 32 translates to an increased sensitivity of sensor 30.

Figure 3:
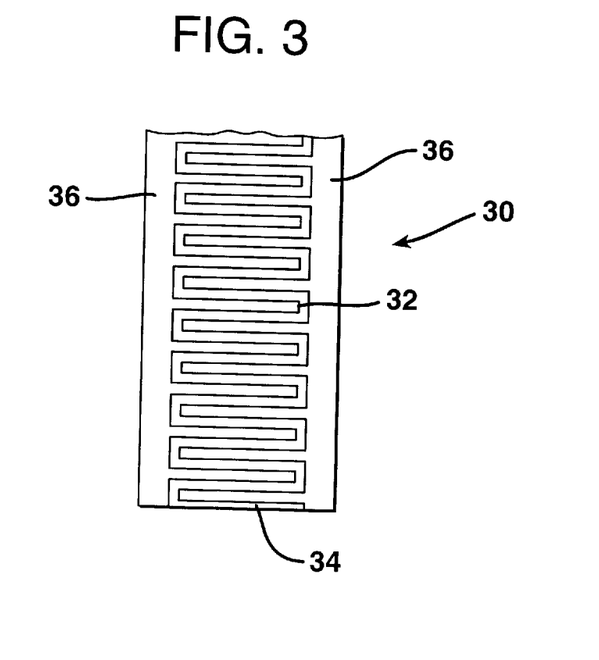
FIG. 3 shows a front view of a preferred electrode configuration for use with this invention.

FIG. 3 shows a front view of a preferred electrode configuration for use with this invention. As can be seen in FIG. 3, conductivity sensor 30 comprises a plurality of electrodes 32. Electrodes 32 are arranged in a coplanar manner parallel to each other in an interlaced network and mounted on a nonconductive substrate 34. To form the network, electrodes 32 extend outwardly from leads 36 toward each other. This arrangement of electrodes 32 allows electrodes 32 to easily detect small changes in the conductivity of the sample 20.

Figure 4:
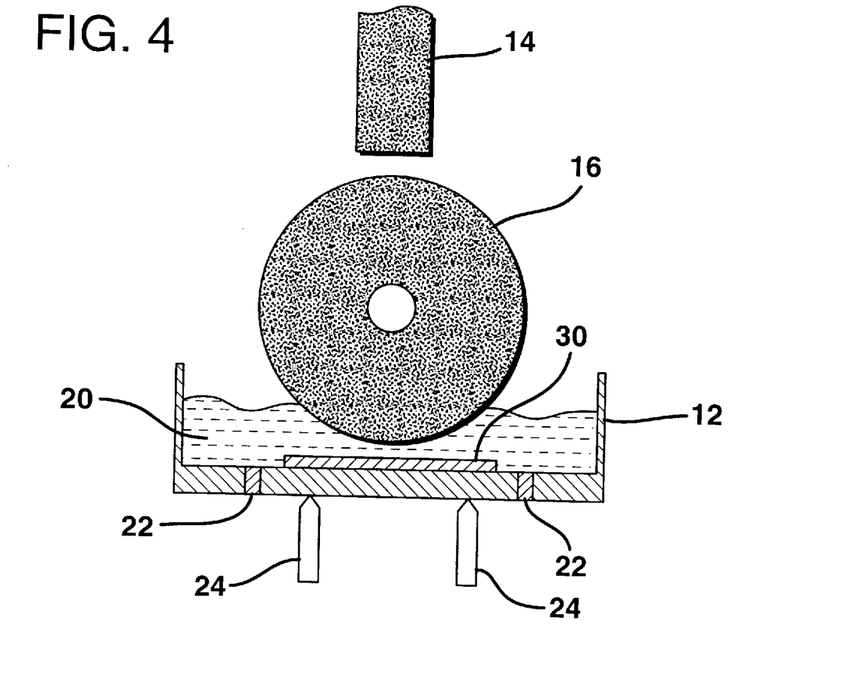
FIG. 4 shows a view of an alternate embodiment of this invention in which the conductivity sensor is mounted on the bottom of the sample vessel of the spectrometer.

FIG. 4 shows a view of an alternate embodiment of this invention in which the conductivity sensor is mounted on the bottom of the sample vessel. As can be seen in FIG. 4, conductivity sensor 30 is mounted on the bottom of sample reservoir 12. In this embodiment, two solder filled holes 22 are formed in sample reservoir 12. This embodiment also includes two pins 24 which make contact with the bottom of sample reservoir 12 so that a current can be supplied to conductivity sensor 30. In this embodiment, conductivity sensor 30 is planar and has an arbitrary geometry. When the spectrometric analysis begins, sample 20 shields conductivity sensor 30 from the sparking activity of the spectrometer while the wear metal and elemental analysis is taking place.

Figure 5:
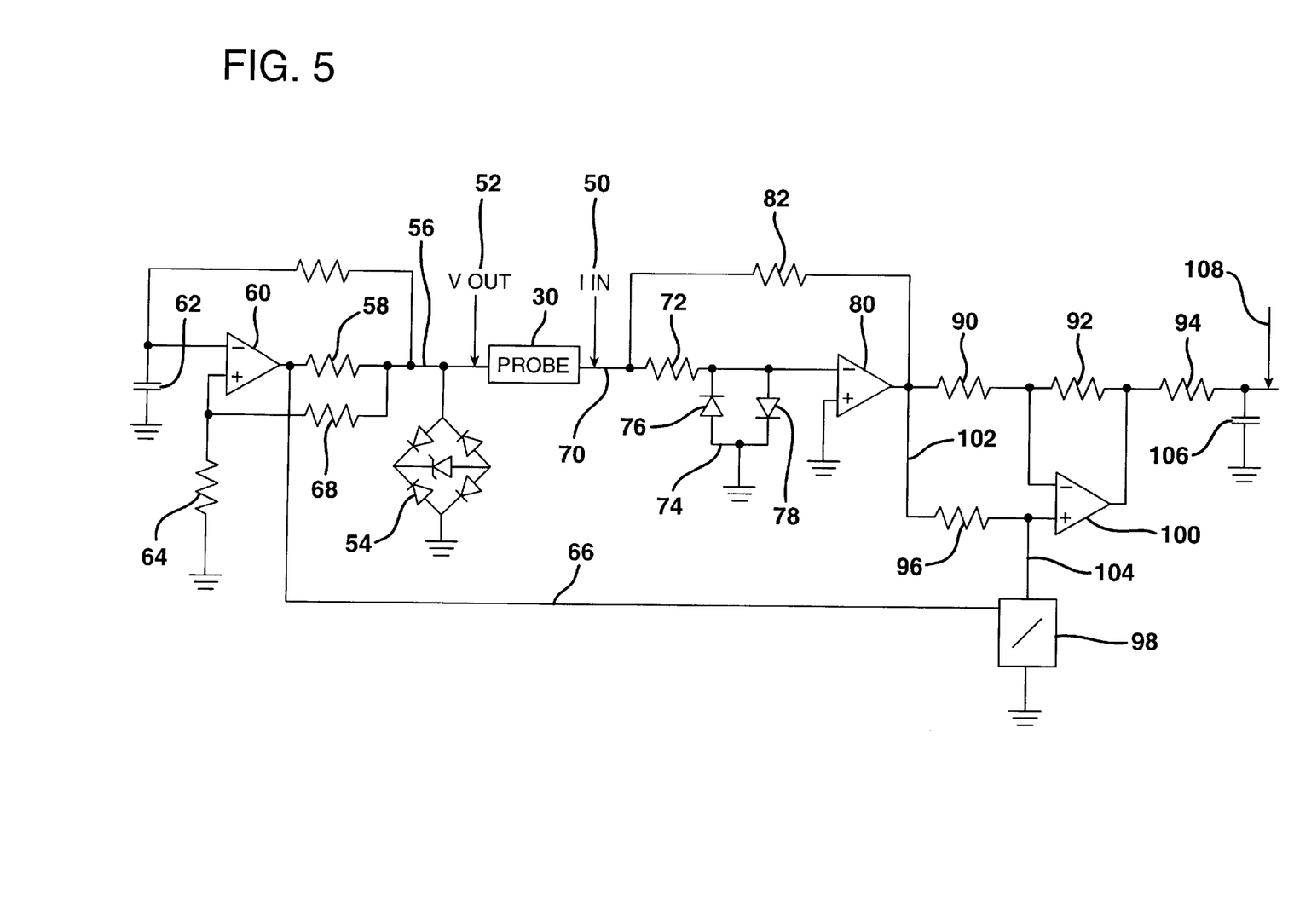
FIG. 5 shows a schematic diagram of the circuitry of the conductivity sensor of this invention.

FIG. 5 shows a schematic diagram of the circuitry of the conductivity sensor of this invention. Probe 30 is located between current input 50 and voltage output 52. Zener diode 54, which provides for the height of the square wave, is connected to ground and lead 56. Lead 56 is connected to resistor 58 which, in turn, is connected in series to operational amplifier 60. Resistor 62 is arranged in a parallel relationship with resistor 58 and operational amplifier 60. The negative lead of amplifier 60 is connected by capacitor 62 to ground. The positive lead of amplifier 60 is split to resistor 64 and lead 66. Resistor 68 is connected in parallel with resistor 58.

As also shown in FIG. 5, lead 70 connects current input 50 with resistor 72 which in turn is connected in series with protection circuit 74 which comprises diodes 76 and 78. Protection circuit 74 is connected to amplifier 80. Resistor 82 is connected in parallel with resistor 72, protection circuit 74 and amplifier 80. Amplifier 80 is connected with the circuitry which rectifies the signal received from probe 30.

The rectification portion of the circuitry includes resistors 90, 92 and 94 solid state switch 98 and amplifier 100. Resistors 90, 92 and 94 are connected in series with amplifier 80. Resistor 96 is connected by lead 102 to amplifier 80. Switch 98 is connected via lead 66 to amplifier 60 and by lead 104 to resistor 96. Amplifier 100 is connected in parallel to resistor 92. Resistor 94 is also connected to capacitor 106 which in turn is connected to ground and signal output 108.

Although it is not shown in FIG. 5, signal output 108 is linked through an adaptor to a data processor which feeds information to a printer. The adaptor is provided because it is contemplated that spectrometers which are currently in use will have to be retrofitted to accommodate the conductivity measurement apparatus of this invention. Because the spectrometer is also connected to the printer, the adaptor acts to switch the input to the printer between the conductivity sensor and the spectrometer.

With this invention, no sample preparation steps are required and the sample can simply be removed from the equipment and placed directly in the sample reservoir of the spectrometer. As a result, the speed of analyses for conductivity and wear metal determinations is increased.

In carrying out the conductivity analysis, a potential is applied to the electrodes. The potential ranges between about +10V and about −10V and preferably ranges between +2.5V and about −2.5V. The voltage of the conductivity sensor is maintained at or between about ±10 volts to ensure that the monitored current is based entirely on the conductivity of the fluid. The smaller scan rate minimizes the possibility of the current produced by the electrochemical activity of antioxidants and thermal-oxidation by-products. The applied frequency of the scan ranges between about 1 and about 100 Hertz in order to minimize capacitance effects. The current flow can range between about 1 nanoamp and about 10 microamperes, with a preferred current flow being less than one microampere. The current flow is detected, rectified, and filtered. Because the current flow tends to be small, an amplification of approximately $1 \times 10^6$ may be used.

During the course of the conductivity analysis, a plurality of data points are generated and analyzed. The data is processed by a microprocessor which converts the data to an readable format and sends the results to a printer. After the analysis is printed out, the control of the printer is returned to the spectrometer. Alternatively, the filtering of the current may be increased to increase the accuracy of the readings and to eliminate the need to collect a large number of data points.

Once the conductivity measurements have been taken, the spectrometer will perform wear metal analysis on the same sample to determine the concentration and elemental constituents in the fluid. This analysis is carried out in a manner familiar to those of skill in the art using any conventional spectrometer which employs a sample reservoir. Preferably, an atomic emission spectrometer, such as a Spectro Junior manufactured by Spectro Oil, is used. As stated above, this analysis is conducted to determine the contamination of the fluid contributed by wear metals from the equipment in which the fluid is used and other elemental constituents.

As described above, once the conductivity analysis and spectrometric analysis are completed, the results of those tests are compared with known values to determine an operating condition of the equipment and an indication of the integrity of the fluid.

EXAMPLE 1

The method of this invention was compared to the method described in U.S. Pat. No. 4,029,554 to Ellison, i.e., the COBRA method. In this test, a T-63 turbine engine stand test was conducted to evaluate a 4-cSt ester base lubricating oil. The lubricant was sampled periodically to determine its physical properties as a function of engine test hours. The COBRA values were obtained by using an apparatus similar to that described in the Ellison patent with the only exception being that the read out on the Ellison apparatus was digital instead of analog. The conductivity values for the same samples were also measured using the method and apparatus described in this specification.

Figure 6:
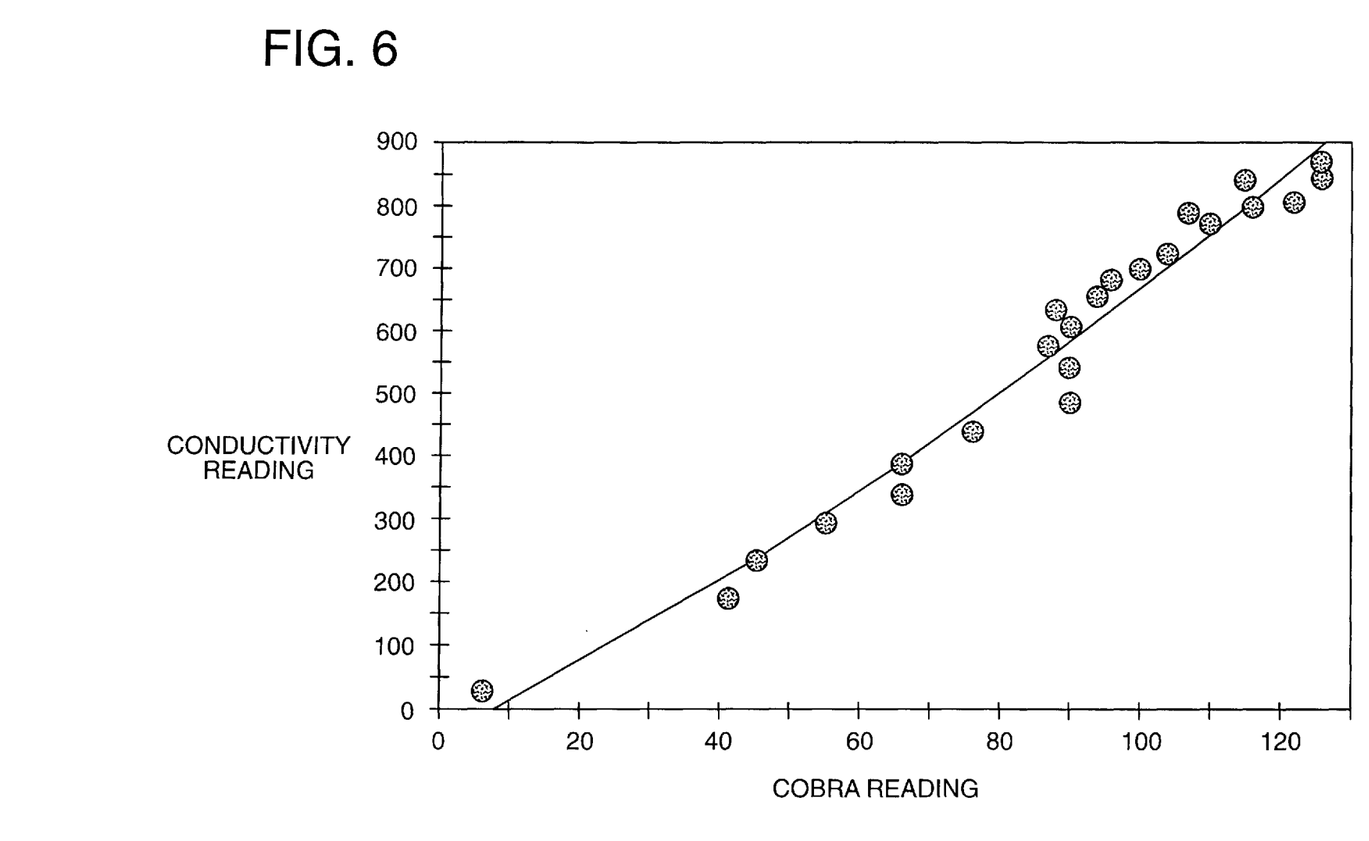
FIG. 6 shows a graph of COBRA values for an oil versus the conductivity values.

As can be seen in FIG. 6, the COBRA values were plotted versus the conductivity values. The graph derived from plotting these points can be interpolated to a relatively straight line indicating that the conductivity method produces values which compare favorably with those produced by the COBRA method.

EXAMPLE 2

A collection of "black oil" samples from gas turbine engines were analyzed using the COBRA method and the method of this invention. A "black oil" has experienced high temperature beyond its capability in an engine and becomes visibly darkened or "black" due to the build-up of carbonaceous material in the oil from the thermal-oxidative stressing. Again, the COBRA values were obtained by using an apparatus similar to that described in the Ellison patent with the only exception being that the read out on the Ellison apparatus was digital instead of analog. The conductivity values for the same samples were also measured using the method and apparatus described in this specification.

Figure 7:
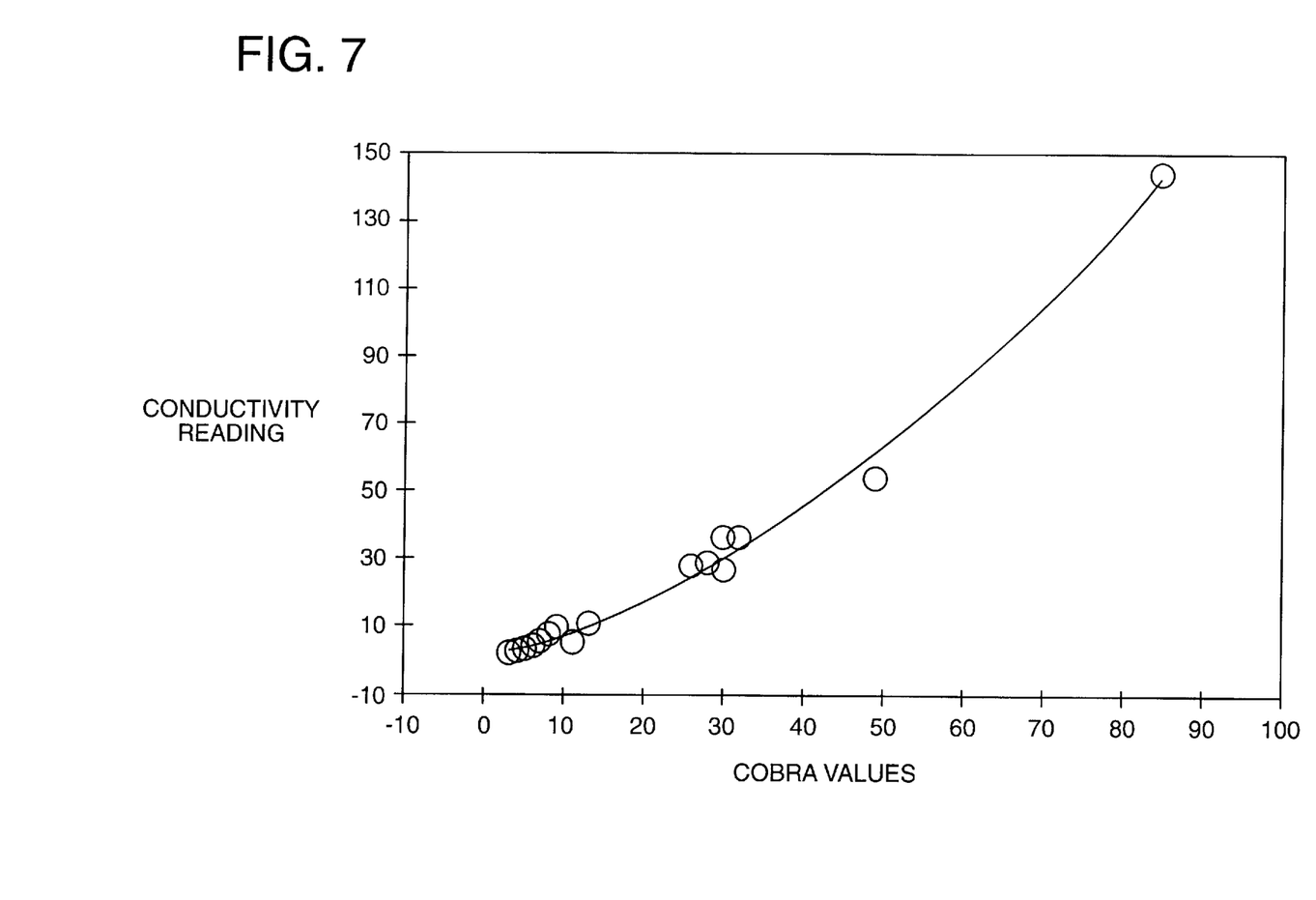
FIG. 7 shows a graph of COBRA values for a used oil sample versus the conductivity values for the same used oil sample.

As can be seen in FIG. 7, a plot of COBRA values versus conductivity values, this plot also can be interpolated into a line having a slope of approximately 1. This indicates that conductivity can reliably measure thermal-oxidative stressing of a lubricant in an authentic used oil sample.

The present invention is useful for monitoring low conductivity fluids which are subject to degradation and/or contamination and which have little or no water content. The invention can be used to analyze such fluids as fuel oils, lubricating oils, lubricating fluids, coolants, hydraulic fluid, transmission fluids, and other fluids. The present invention can be used to monitor fluids in many different types of equipment, for example, gas turbine engines, combustion engines, transmission systems, hydraulic systems, gear boxes, and operating machinery. Other uses and applicable fluids will be apparent to those skilled in the art.

One skilled in the art will appreciate that the invention is not limited to the precise method and apparatus described herein, and that changes can be made to this apparatus and method without departing from the scope of the invention, which is defined in the appended claims.

What is claimed is:

1. A method for testing a fluid which is subject to degradation and for determining the operating condition of a piece of equipment in which the fluid is used comprising the steps of:

bringing at least two electrodes into contact with a sample of a fluid;

applying a square voltage wave form to the electrodes at a predetermined scan range and scan rate to cause a current to flow between the electrodes;

monitoring the current at the electrodes to determine a current output signal;

using the current output signal to measure the conductivity of the fluid; and analyzing the sample to determine a content of wear metals and elemental constituents in the sample, all while maintaining said fluid at ambient temperature.

2. The method of claim 1 wherein the scan range is from about +10V to about −10V.

3. The method of claim 2 wherein the scan range is from about +2.5V to about −2.5V.

4. The method of claim 3 wherein the scan rate is about 1 to about 100 Hertz.

5. The method of claim 4 further including the step of comparing the measured conductivity of the sample with a known conductivity value for the fluid to determine the integrity of the fluid and an operating condition of the equipment.

6. The method of claim 5 wherein the step of analyzing the sample takes place in a spectrometer.

7. The method of claim 6 wherein the spectrometer is an atomic emission spectrometer.

8. The method of claim 7 wherein the fluid is a low conductivity fluid.

9. The method of claim 8 wherein the fluid is selected from the group consisting of fuel oils, lubricating oils, lubricating fluids, coolants, hydraulic fluids, and transmission fluids.

10. The method of claim 1 wherein the electrodes are arranged in a coplanar, interlaced network.

11. The method of claim 10 wherein the network of electrodes is removable from the fluid after the analysis is completed.

12. A method for testing a fluid which is subject to degradation and for determining the operating condition of a piece of equipment in which the fluid is used comprising the steps of:

bringing a plurality of electrodes into contact with a sample of a fluid to be analyzed, the electrodes being arranged in an interlaced network;

applying a square voltage wave form to the electrodes at a scan range from about +2.5V to about –2.5V and scan rate of about 1 Hertz to cause a current to flow between the electrodes in the network;

monitoring the current at the network to determine a current output signal; using the current output signal to measure the conductivity of the fluid; and analyzing the sample to determine a content of wear metals and elemental constituents in the sample, all while maintaining said fluid at ambient temperature.

13. The method of claim 12 further including the step of comparing the measured conductivity of the sample with a known conductivity value for the fluid to determine an operating condition of the equipment and an indication of the integrity of the fluid.

14. The method of claim 13 wherein the step of analyzing the sample takes place in an atomic emission spectrometer.

15. The method of claim 14 wherein the fluid is selected from the group consisting of fuel oils, lubricating oils, lubricating fluids, coolants, hydraulic fluids, and transmission fluids.

* * * * *